United States Patent [19]

Rose

[11] 4,285,968
[45] Aug. 25, 1981

[54] PESTICIDAL CONCENTRATE WITH STABILIZING AGENT

[75] Inventor: Wayne B. Rose, Merriam, Kans.

[73] Assignee: Cutter Laboratories, Inc., Berkeley, Calif.

[21] Appl. No.: 879,187

[22] Filed: Feb. 21, 1978

[51] Int. Cl.$^3$ ............................................. A01N 47/10
[52] U.S. Cl. ..................................................... 424/300
[58] Field of Search ........................................ 424/300

[56] References Cited

U.S. PATENT DOCUMENTS

| | | | |
|---|---|---|---|
| 3,111,539 | 11/1963 | Böcker et al. | 424/300 X |
| 3,342,673 | 9/1967 | Kaufman et al. | 424/300 X |
| 3,408,323 | 10/1968 | Hackney | 424/83 X |
| 3,658,959 | 4/1972 | Inks | 424/300 |
| 4,048,302 | 9/1977 | Coleman et al. | 424/78. |

OTHER PUBLICATIONS

Chemical Week, Apr. 12, 1969, pp. 47 & 48.

*Primary Examiner*—Allen J. Robinson
*Attorney, Agent, or Firm*—James A. Giblin

[57] ABSTRACT

Pesticidal concentrate comprising o-isopropoxyphenyl methylcarbamate and an acidifying agent dissolved in a liquid, water soluble, dispersion medium.

4 Claims, No Drawings

PESTICIDAL CONCENTRATE WITH STABILIZING AGENT

BACKGROUND OF THE INVENTION

1. Field

This disclosure is concerned generally with the manufacture and use of pesticidal solutions and specifically with an easy-to-use pesticidal concentrate which, when dissolved in water, demonstrates excellent long term stability.

2. Prior Art

The pesticidal substance o-isopropoxyphenyl methylcarbamate is a well known insecticide and arachnidicide, the manufacture and use of which is described in U.S. Pat. No. 3,111,539 to E. Böker et al. Although the pesticide may be applied to the skin or coats of domestic animals in a variety of forms (e.g. as a powder, in a flea collar, flea stick, as a liquid, etc.), a very effective and preferred method of application involves preparing an emulsion, suspension, or solution of the pesticide which can be used to treat an animal infested with fleas, ticks, mites, and the like. Typically, such emulsions, suspensions, or solutions can be sponged or poured onto the animal or the animal can be dipped into the preparation for intimate and uniform distribution of the pesticide throughout the animal's coat.

Since the carbamate has a relatively low solubility in water, it had been a common practice to initially dissolve the carbamate in a compatible organic solvent to which a wetting agent or a surfactant is also added. In use, that concentrate was then dispersed in water to form an emulsion which was then applied to the coat of the animal. Because of objectional odors associated with the use of common organic solvents such as xylene, toluene, various naphthalenes, and kerosene, some of which may also be toxic, such solvents have been avoided where possible. Although a variety of surfactants may be used to help disperse the carbamate in an aqueous solution, the use of many surfactants results in a product which leaves an undesirable oily or sticky film on the coats of treated animals.

The carbamate has also been available as a wettable powder consisting of the active ingredient dispersed in a finely divided inert carrier to which a wetting agent and acidifying agent such as citric acid have been added. Such powders, however, tend to cause dusting and toxicity problems.

It can be appreciated that many of the above disadvantages are based primarily on the relatively low aqueous solubility of the carbamate. Even though the carbamate is pesticidally effective in relatively dilute concentrations in water (e.g. 0.125 wt.%), the direct mixing of the carbamate in water is inconvenient and time-consuming, especially in situations where only one animal is to be treated on a one-time basis. Because of this, it had become common to make the carbamate available in organic solutions or emulsion form so that the active ingredient could be conveniently diluted with water prior to use.

The above disadvantages associated with the low aqueous solubility of the carbamate and the consequent use of organic solvents and and emulsifiers have been avoided to a large extent by the recent discovery that the carbamate can be initially dissolved in a water soluble, essentially odorless, dispersion medium such as polyethylene glycol to form a conveniently storable concentrate, readily dilutable with water to form a non-oily product. One such dual solvent system is described in U.S. Pat. No. 4,048,302 to W. R. Coleman et al. The concentrate of that disclosure is prepared by dissolving about 5 to 15 weight percent of the carbamate in a compatible, non-toxic, essentially odorless, water soluble solvent such as polyethylene glycol (peg). This concentrate may be stored until needed at which time it is dissolved in about 10 to 50 parts water to form a final solution which can be applied directly to an animal's coat or into which an animal can be dipped.

Although the disclosed carbamate-polyethylene glycol concentrate provides a quick and convenient method of delivering the active ingredient into an aqueous solution to yield an essentially odorless, non-toxic, non-oily, final product, that product has a rather limited stability and must be used within a short time after preparation. Quite surprisingly, it has now been found that the stability of such products can be significantly enhanced by providing a novel pesticide concentrate, details of which are described herein.

SUMMARY OF THE INVENTION

The pesticidal concentrate of this disclosure comprises o-isopropoxyphenyl methylcarbamate and an acidifying agent dissolved in a liquid, water-soluble dispersion medium. Prior to use, an aliquot of the concentrate is dissolved in a quantity of water sufficient to assure that the final concentration of the o-isopropoxyphenyl methylcarbamate ranges from about 0.1 to 0.2 weight percent of the aqueous solution. The amount of acidifying agent in the concentrate is sufficient to assure that the pH of the aqueous solution is maintained at or below about 7.0, preferably at or below about 5.0. The water-soluble dispersion medium of the concentrate should be present in an amount sufficient to assure dissolution of substantially all the carbamate. In a preferred embodiment the concentrate comprises, on a weight percent basis, about 5 to 15% o-isopropoxyphenyl methylcarbamate, 79 to 94% of a liquid ethylene glycol polymer as the dispersion medium, and 1 to 6% citric acid or a salt thereof as the acidifying agent.

SPECIFIC EMBODIMENTS

Very important to the concentrate is the inclusion of an acidifying agent in a quantity sufficient to assure an acidic solution when the concentrate is diluted with water to form an aqueous solution of an effective amount of the carbamate. The acidifying agent must not be detrimental or toxic to any animal treated with the final aqueous solution of the carbamate, dispersion medium, and acidifying agent. In addition, the acidifying agent should have no detrimental effect on the carbamate or the dispersion medium in the concentrate or final aqueous (diluted) form. The amount of acidifying agent must be sufficient to result in a final aqueous solution having a pH of 7.0 or less (preferably about pH 5.0 or less) while not having any of the above detrimental effects on either an animal to be treated or the other ingredients. Among the acidifying agents which meet the above requirements, a preferred agent is a weak acid such as citric acid which, in general, will not lower the pH below about 3.0. A preferred amount of citric acid in the concentrate ranges from about 1 to 6wt. %.

The dispersion medium must be very water soluble and be present in the concentrate in sufficient amount to assure dissolution of substantially all of the carbamate present at room temperature. Like the acidifying agent, the dispersion medium should have no detrimental effect on the animal to be treated in its diluted (aqueous) state and no detrimental or inactivating effect on the carbamate in the concentrate or diluted state. In addition, the dispersion medium must be stable in the concentrate and, when diluted with water, it must not be reactive with the other components of the concentrate.

It can be appreciated that the dispersion medium acts as a convenient delivery vehicle for the carbamate which, if mixed directly with the water, would require added time and effort to disperse. By initially dissolving the carbamate in a water-soluble dispersion medium, the subsequent dispersion of the carbamate into the water is accomplished conveniently and relatively quickly. Although a number of dispersion mediums which meet the above requirements are available, (e.g. methanol, ethanol, isopropanol, dipropylene glycol monomethyl ether, etc.), a preferred medium is polyethylene glycol, preferably in a molecular weight range which permits convenient dissolution of sufficient quantities of the carbamate and acidifying agent to result in a concentrate which, when diluted with water, results in an aqueous solution having a pH of 7.0 or less and having dissolved therein a pesticidally effective amount of the carbamate.

In general, the amount of carbamate in the concentrate ranges from about 5 to 15 weight percent with the dispersion medium ranging from about 79 to 94 weight percent. To be pesticidally effective yet safe, the final concentration of the carbamate in the aqueous solution should range from 0.1 to 0.2 weight percent, preferably about 0.125 wt. %. Although 0.2 wt. % is a practical upper limit because of solubility considerations, it is thought that, with repeated applications, a carbamate concentration as low as 0.05 wt. % would be effective. I have found that a very practical concentration of the carbamate in the dispersion medium is about 8% by weight with the dispersion medium and acidifying agent making up the remaining 92%.

The amount of water with which a given amount of the concentrate is diluted should be sufficient to result in a final aqueous solution of an effective amount of the carbamate (0.1 to 0.2 wt.%) at a pH of 7.0 or less with dissolution of substantially all the dispersion medium of the concentrate.

EXAMPLES

Preparation of Concentrate:

A very preferred concentrate comprises a solution of the carbamate and citric acid as the acidifying agent dissolved in polyethylene glycol (peg) as the water soluble dispersion medium. The concentrate was prepared as follows: 8 g of the o-isopropoxyphenyl methylcarbamate are added to 88 g of polyethylene glycol liquid, the peg polymer having an average molecular weight of about 400. The mixture is stirred until the carbamate is fully dissolved and 4 g of citric acid is added to the carbamate-peg solution which is also stirred until the citric acid is dissolved. The mixing is done at 60° C. and the reagents may be mixed simultaneously.

Dilution of the Concentrate:

In a typical application two ounces of the above concentrate liquid are added to one gallon of tap water, preferably warm (about 25° C.), which is then stirred to assure even distribution of the concentrate. The above dilution results in an effective carbamate concentration of about 0.125 wt. percent, an amount effective to kill ticks and fleas on dogs and cats.

Application of the Diluted Solution:

An animal thought to be infested with fleas, ticks, etc., may be dipped into the solution, with head above the solution, for about 5 to 10 seconds. Alternatively, the diluted solution may be poured on the animal until the hair coat is thoroughly wet to the skin. It has been found that the initial kill of fleas and non-engorged ticks is rapid but 24 to 48 hours may be required for complete killing of the engorged ticks. In that case, for residual activity of the carbamate, the solution is allowed to dry on the animal. Although the diluted solution may be applied as needed, it is generally not applied more often than weekly.

Stability Studies:

The effectiveness of including an acidifying agent in the concentrate for convenient preparation of a final aqueous solution was demonstrated by studying the effect of pH over time on the utility of the carbamate aqueous solution. Test solutions were prepared by adding 19 g of a wettable powder (Sendran ® 50 powder) of the carbamate to one gallon of water adjusted to each indicated pH with either citric acid or 1 N KOH. Carbamate concentrations were determined via infrared method or via gas chromatography (GLC). Those solutions (or suspensions) of carbamate in which an acidifying agent was not present maintained 90% carbamate activity for only 0.87 days at pH 8.0 and only 0.13 days at pH 9.0, whereas the carbamate solutions acidified with the citric acid to pH 7.0 and 5.0 retained 90% carbamate activity for 4.6 and 131 days respectively. At pH 6.0, the carbamate retained 90% activity for 96 days. The above results demonstrate the dramatic effect of the acidifying agent on long term stability. The '90% days were determined by linear regression. It is thought that the carbamate tends to decompose in an alkaline environment. The results are summarized in the Table.

TABLE

| Carbamate Concentration (wt. %) as a Function of pH and Time | | | | |
|---|---|---|---|---|
| | pH 5 | pH 6 | pH 7 | pH 8 | pH 9 |
| Initial | 0.29 | 0.28 | 0.29 | 0.28 | 0.21 |
| After 1 Day | 0.28 | 0.27 | 0.27 | — | 0.10 |
| After 3 Days | 0.28 | 0.27 | 0.26 | 0.16 | 0.07 |
| After 1 Week | 0.28 | 0.28 | 0.25 | 0.10 | Discontinued |
| After 2 Weeks | 0.28 | 0.27 | 0.23 | Discontinued | " |
| After 3 Weeks | 0.28 | 0.28 | 0.21 | " | " |
| After 4 Weeks | 0.28 | 0.27 | 0.20 | " | " |
| After 5 Weeks | 0.28 | 0.26 | 0.19 | " | " |
| After 6 Weeks | Discontinued | | 0.17 | " | " |
| $t_{90\%}$ days | 131 | 96 | 4.6 | 0.87 | 0.13 |

Given the above disclosure, it is thought numerous variations will occur to those skilled in the art. Accordingly it is intended that the above examples should be construed as illustrative only and that the scope of the invention disclosed herein should be limited only by the following claims.

I claim:

1. A pesticidal concentrate comprising o-isopropoxyphenyl methylcarbamate and citric acid or a salt thereof dissolved in a liquid water soluble dispersion medium selected from the group consisting of methanol, ethanol, isopropanol, dipropylene glycol monomethyl ether, and polyethylene glycol, the amount of the dispersion medium being sufficient to assure dissolution of substantially all of the carbamate at room temperature and, the amount of the citric acid or salt thereof being sufficient, when the concentrate is diluted to result in a pesticidally effective amount of the carbamate with water, to result in an aqueous solution having a pH of 7.0 or less.

2. The concentrate, as claimed in claim 1, wherein the amount of citric acid or salt thereof ranges from about 1 to about 6 weight percent, the dispersion medium is polyethylene glycol, and the amount of polyethylene glycol polymer ranges from about 79 to 94 weight percent.

3. The concentrate, as claimed in claim 1, wherein the amount of o-isopropoxyphenyl methylcarbamate ranges from about 5 to 15 weight percent.

4. The concentrate, as claimed in claim 2, wherein the amount of o-isopropoxyphenyl methylcarbamate ranges from about 5 to 15 weight percent.

* * * * *